Figure 5:
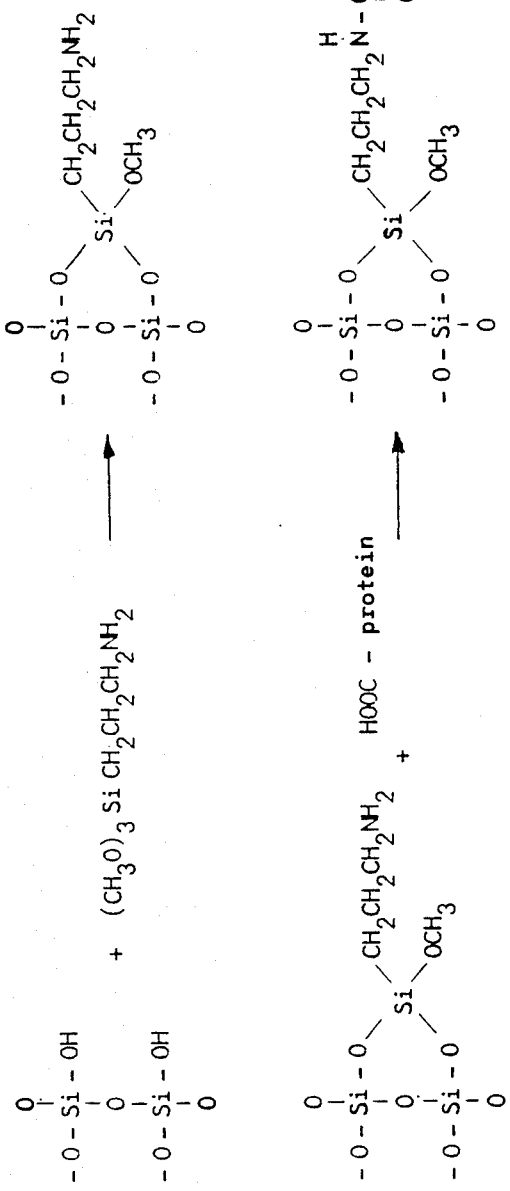

United States Patent [19]

Barendz et al.

[11] Patent Number: 4,860,573
[45] Date of Patent: Aug. 29, 1989

[54] COMPOSITE SUBSTRATE, INTENDED FOR AN APPARATUS FOR QUANTITATIVE DETECTION OF A COMPONENT PRESENT IN A GAS OR LIQUID

[75] Inventors: Anton W. Barendz, Katwijk aan Zee; Maarten S. Nieuwenhuizen, The Hague, both of Netherlands

[73] Assignee: Nederlandes Organisatie voor Toegepast-Natuurwetenschappelijk Onderzoek TNO, The Hague, Netherlands

[21] Appl. No.: 61,281
[22] PCT Filed: Oct. 3, 1986
[86] PCT No.: PCT/NL86/00033
§ 371 Date: Jul. 17, 1987
§ 102(e) Date: Jul. 17, 1987
[87] PCT Pub. No.: WO87/02135
PCT Pub. Date: Apr. 9, 1987

[30] Foreign Application Priority Data

Oct. 3, 1985 [NL] Netherlands ............ 8502705

[51] Int. Cl.$^4$ ............................................ G01N 29/00
[52] U.S. Cl. ............................................ 73/23
[58] Field of Search ............................................ 73/23

[56] References Cited

U.S. PATENT DOCUMENTS

| | | |
|---|---|---|
| 3,831,432 | 8/1974 | Cox ............................................ 73/23 |
| 4,321,228 | 1/1982 | Wohltjen ............................ 73/23 X |
| 4,361,026 | 11/1982 | Muller et al. ............................ 73/23 |
| 4,381,922 | 5/1983 | Frey et al. ............................ 73/23 X |
| 4,562,725 | 1/1986 | Oka et al. ............................ 73/29 |
| 4,596,697 | 6/1986 | Ballato ............................ 73/23 X |
| 4,598,224 | 7/1986 | Ballato ............................ 73/23 X |
| 4,637,987 | 1/1987 | Minten et al. ............................ 73/23 X |
| 4,674,319 | 6/1987 | Muller et al. ............................ 73/23 |
| 4,730,478 | 3/1988 | Gedeon ............................ 73/23 |
| 4,735,081 | 4/1988 | Luoma et al. ............................ 73/23 |

Primary Examiner—Stewart J. Levy
Assistant Examiner—Joseph W. Roskos
Attorney, Agent, or Firm—Beehler & Pavitt

[57] ABSTRACT

A substrate for an apparatus for quantitative detection of a component present in a gas or liquid, in which substrate elastic vibrations can be generated, said substrate being provided with a surface layer adapted to bond said component, so that the vibration behavior of said layer is changed. At least the surface portion of said substrate consists of a substance with active sites (A) for covalent bonding situated at its free surface, to which sites (A) molecules of a substance (X) are covalently bonded which, on the other hand, possess active sites (B) for selectively and reversibly bonding by means of a coordinative bond of the molecules of the component (G) to be detected. In particular between each active site (A) of the substrate and a molecule of the component bonding substance (X) a molecule of a coupler (K) can be inserted, which is covalently bonded to an active site (A) of said substrate, and, on the other hand, is bonded by means of a second bond (C) with a molecule of the component bonding substance (X), said second bond being a substantially covalent bond or a substantially coordinative bond. The component bonding substance (X) can be a substance in the form of an inclusion compound ($X_1$), a complexing compound ($X_2$), a metal ion cluster ($X_3$), or an enzyme ($X_4$). The coupler (K) can be formed by a trialkoxysilane compound with general formula $(RO)_3Si(CH_2)_n\text{-}Y$, in which Y is adapted to provide the covalent or coordinative bond (C) with the component bonding substance (X), and comprises an active group, which coupler (K) can be a compound of the following kind (Formula I).

10 Claims, 3 Drawing Sheets

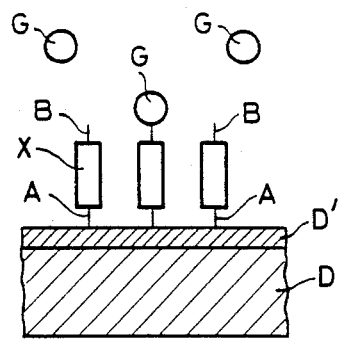
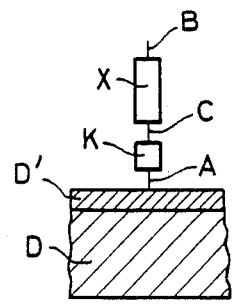
FIG: 1A.  FIG: 1B.
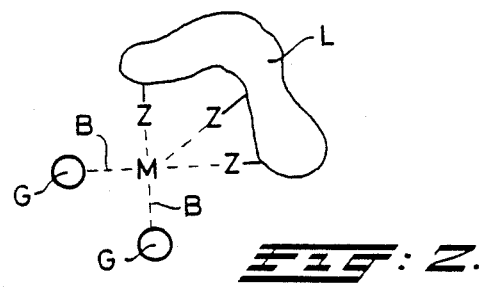
FIG: 2.
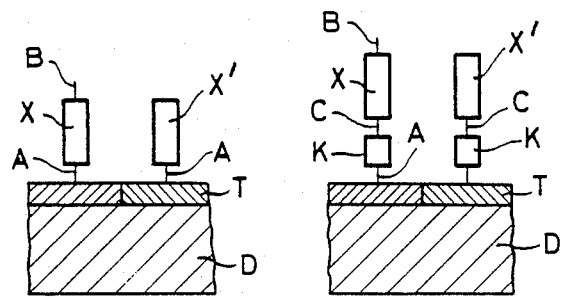
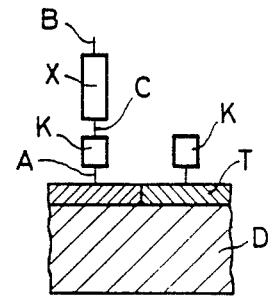
FIG: 3A.  FIG: 3B.  FIG: 3C.

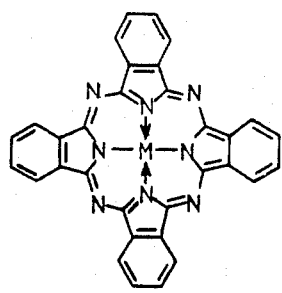
M(II) phthalocyanine
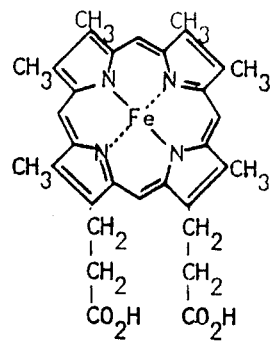
Fe(III) deuteroporphyrine
ferrocene
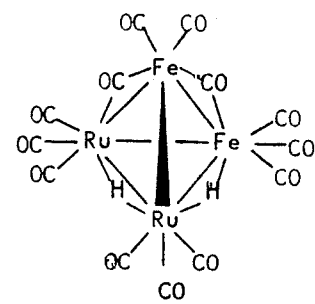
$Ru_2Fe_2H_2(CO)_{13}$ cluster
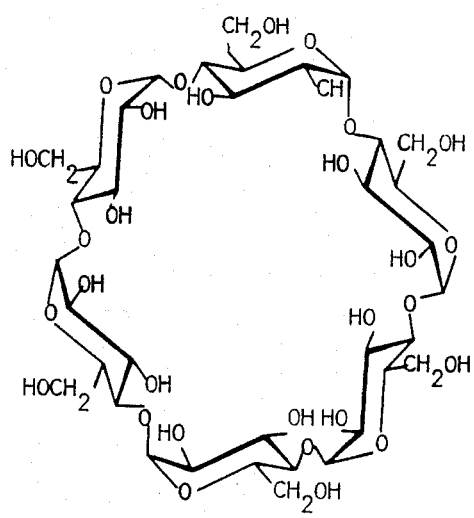
α - cyclodextrine
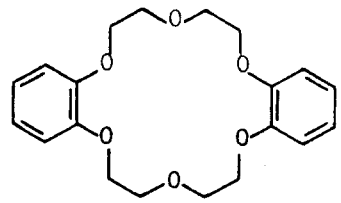
dibenzo - 18 crown ether - 6
FIG. 4.

COMPOSITE SUBSTRATE, INTENDED FOR AN APPARATUS FOR QUANTITATIVE DETECTION OF A COMPONENT PRESENT IN A GAS OR LIQUID

There is a large need for apparatuses for quantitative detection of a noxious gas or vapour in a mixture, e.g. in exhaust gases of internal combustion motors or chemical industries, poisonous vapours in containers, reaction chambers, hothouses or the like, as well as poisonous gases in the air, e.g. for military purposes.

Such apparatuses should be small, robust and relatively cheap, but should, nevertheless, operate dependably, and moreover requirements in respect of the sensitivity, response speed, stability etc. should be satisfied.

Moreover an apparatus intended for this purpose should be selective for a given component (or a restricted number of related components), and should also operate in such a reversible manner that concentration variations of the substance to be detected can be followed rapidly and dependably, and a continuous measurement can take place.

For a quantative detection of components present in the liquid or gas apparatuses are known, comprising a substrate in which, by means of a piezo-electric transducer, elastic vibrations can be generated, said substrate being provided with a surface layer which is able to bond said component if it is being contacted with said layer, so that the vibration behaviour of said layer is changed, and said elastic vibration is transformed again into an electric vibration by means of a piezo-electric transducer so as to detect the change in the vibration behaviour of said layer. To that end reference can be made to U.S. Pat. No. 4,312,228. In this known apparatus the component to be detected is absorbed in the surface region of the substrate, the absorbed mass changing the vibration behaviour of the surface layer of said substrate, and in particular the propagation velocity of the elastic surface wave generated in said layer, and said wave an be detected by means of a piezo-electric transducer which transforms said vibration into an electric signal. The frequencies used therefor can be very high, so that, in view of the propagation velocity of the elastic vibration in the substrate, a very small distance can contain a very large number of wavelengths, so that the transit time variations can be determined very well.

In this known apparatus, a polymer layer is provided on the substrate surface which serves as an absorbent for gases.

This known apparatus is not suitable for the abovementioned purposes. In the first place absorption is not very selective, and moreover, the reversibility of absorption is insufficiently fast for obtaining a quick adaptation to concentration variations. Moreover the polymer layer is relatively thick and does not form an essential part of the transfer path of the vibration which is mainly propagated along the substrate surface. This unfavourably influence the sensitivity. Moreover it is very difficult to produce such layers with a reproducable thickness and structure.

It is an object of the invention to provide a substrate for such an apparatus which is suitable for the abovementioned purposes, said substrate being characterised in that at least the surface portion thereof consists of a substance with active sites for covalent bonding situated at its free surface, and in that, in said sites, molecules of a substance are covalently bond, said molecules possessing, on the other hand, active sites for selectively and reversibly bonding molecules of the component to be detected by means of a coordinative bond.

The coordinative bond with the component to be detected is relatively weak, so that the molecules of the component to be detected can be released relatively easily when the concentration of said component in the vicinity of the substrate is reduced, but said bond is strong enough for fixing said molecules, during the measurement, to the vibrating substrate. Such a layer is extremely thin, and comprises a large number of very regularly distributed bonding sites for said component, and said bond can be made very selective, and the mass variation in respect of the mass of the layer is substantial so that a sensitive and also reproducible measurement can be obtained. Said bonding molecules are, on the other hand, covalently, bonded to the substrate, which bond is very strong, so that the bonding substance remains strongly connected to the substrate, and obtains, at the same time, a very good and uniformly distributed vibration coupling with said substrate.

The molecules of said bonding substance are relatively large, which can unfavourably influence the bond with the substrate. It can, therefore, be advisable to insert, between the active sites of the substrate and said bonding substance molecules, a coupler which, on the one hand, is covalently bonded to the active sites of the substrate, and, on the other hand, is bonded by means of a second bond to the bonding substance molecules. Said coupler forms therefore an adaptation between the available active sites of the substrate and the extremity of the bonding substance molecules directed towards the substrate.

The second bond can be also a substantially covalent bond, in order to form a strong connection with the bonding molecule. However it can sometimes be favourable to use, for the second bond, a bond of the cooredinative kind, and then one of the active sites available for bonding the component to be detected can be used. The weaker bond enables to remove the bonding substance and to replace it by a different one, and sometimes such a bond can increase the selectivity of the remaining active sites.

In order to increase the bonding power for the component to be detected, it can sometimes be favourable to connect a stack of molecules of the bonding substance with a common active site of the substrate, each of said molecules having active sites for bonding said component.

As the active sites of the substrate, for instance OH groups at the surface of the substrate can be considered. In particular the substrate or a surface layer thereof consists of a metal oxide.

It is preferred to use as the substrate a silicon wafer convered with a silicon oxide layer, said silicon oxide comprising the OH groups. Manufacturing such wafers is known from the semiconductor technology, and obtaining oxide layers with the desired thickness and structure does not offer any difficulties anymore. Moreover electric (micro) circuits can be formed on such a wafer by means of the current semiconductor techniques, said circuits being required for signal generation and processing.

The surface part of the substrate can also consist of a piezo-electric metal oxide as, for instance, ZnO, which serves for generation and transforming the elastic vibration as well as for bonding the bonding substance. If, on the other hand, such piezo-electric oxide layers are only provided at the transducer electrodes, it is advisable to treat the surface thereof so that it becomes insensitive for the component to be detected. This can be done in substantially the same manner as mentioned for bonding to the surface layer of a substance sensitive for this component, but then a similar substance without active sites for bonding said component is to be used.

For these purposes various kinds of compounds are suitable which will be mentioned below in more detail.

The invention will be elucidated below in more detail by reference to a drawing, showing in:

FIGS. 1A and B diagrammatic representations of a substrate with an active layer bonded thereto, for elucidating the principle on which the invention is based;

FIG. 2 a diagrammatic representation for elucidating the concept of corrdinative bonding;

FIGS. 3A, B and C representations corresponding to FIG. 1 for elucidating the manner in which a part of the active surface of such a substrate can be made inactive;

FIG. 4 a number of structural formulae of compounds suitable for the present purposes; and FIG. 5 reaction equations for elucidating the attachment of such an active layer to the substrate.

In FIG. 2A a substrate in the form of a wafer D is diagrammatically shown. This wafer is provided with known piezo-electric means not shown, by means of which acoustic surface waves can be generated near its free surface. A surface portion D' of the wafer consists of a metal oxide comprising active sites A provided by OH groups present in the oxide, by means of which convalent bonds can be formed.

In particular the wafer D consists of Si, and the surface layer of $SiO_2$. However, it is also possible to form a layer D' from, for instance, ZnO which is piezo-electric, and can be used also for forming vibration sources and sensors.

Molecules X are covalently bonded to these active sites A, said molecules having at least one active site B, the latter sites B being suitable for forming a so-called coordinative bond with a molecule G of a component of a gas or liquid to be contacted with said substrate D, the latter bond being, in particular, more or less selective for said component.

For elucidating the concept of coordinative bonding, reference is made to FIG. 2. Therein L represents a so-called ligand which is neutral or charged, and which is, in particular, an organic compound. So-called donor atoms Z will, then, interact with a metal ion M, and one or more free sites B of the latter will remain which are suitable for bonding the component G to be detected.

A coordinative bond is less strong than a chemical bond as, for instance, the covalent bond, but is stronger than an adsorption bond (van der Waals forces). This is very favourable for the present purposes. For, if in the surface region of the substrate an acoustic wave is generated, the magnitude of the additional mass of attached molecules G should be unambiguously derivable from the change experienced by such a wave at a consequence of said additional mass, so that the bond between the molecules G and the substrate D should be sufficiently strong. On the other hand said bond should not be so strong that the molecules G can only be released difficultly or not at all, so that, then, such a device would not be usable again after a measurement. However the coordinative bond can be sufficiently easily broken so as to obtain always an equilibrium condition between the free molecules G near the substrate surface and the attached molecules, from which, of course after calibration of the apparatus, the concentration of the free molecules G can be derived in a dependable manner.

FIG. 1B shows the case that the molecules X as such can not or not sufficiently attach to the active sites A. With these active sites A, molecules K of a coupler are now covalently bonded, the latter, on the other hand, being able to bond the molecules X by means of bonds C. The bonds C can be covalent bonds as well, but can also be of an other kind, and in particular coordinative bonds, provided that said bond is sufficiently strong for the purposes in view.

It is possible then to begin by bonding the molecules K to the molecules X, thus producing complex molecules which, as far as the effect aimed at is concerned, do not differ from the simple molecules X, and can be attached as such to the active sites A of the substrate. However it can be favourable to provide first the substance K on the surface of the substrate D, and only thereafter the substance X. This can lead to a simplification of the process and an improvement of the effect.

Attaching the molecules G should only take place in those points where said molecules can effectively influence the produced acoustic waves. It is often desired not to expose the piezo-electric transducers used for generating and receiving the waves to said attachement. If said transducers, as mentioned above, comprise a ZnO layer, bonding X or K resp. will take place there too.

It is, of course, possible not to provide X near said transducers, but then it cannot be avoided that, in the free sites A, other substances are bonded in an uncontrollable manner.

FIG. 3 shows different solutions for avoiding the latter. At A is indicated that at a transducer T a substance X' is bonded to the sites A, which substance does not possess active sites B, Case B corresponds with case A, but now a layer K has been provided first over the whole surface. This can simplify the separate bonding of the substances X and X' if the attachment of X and X' to K by means of the bonds C is simpler than the direct attachment by means of the bonds A. In case C the layer K is, again, provided everywhere, but the substance X' is left out. This is possible if the bonds C give rise to a smaller extent to undesired attachment of other substances.

For X and K many different substances are already available. It will be clear that the choice of a substance X will be determined, in the first place, by the character of the component G to be detected, by the desired selectivity and the like, and in the case of a direct bond to the substrate D also by the character of the latter. The choice of the coupler K is, of course, determined by the character of the chosen substance X and the substrate D, and by the desired strength of the bond C.

For X the following substances are, for example, usable:

$X_1$: substances in the form of an inclusion compound, activated or not with metal ions, e.g. a cyclodextrin or a crown ether;

$X_2$: complexing compounds;

$X_3$: metal ion clusters; or $X_4$: enzymes.

Examples of $X_2$ are phthalocyanine compounds, comprising H, Si or a metal ion, ferrocene compounds or compounds of this kind with a metal other than iron, and $\beta$-diketones or aminopolycarboxylates such as, for example EDTH, comprising a metal ion and, in particular, a lanthanide ion.

As the coupler K, a trialkoxysilane compound with the general formula $(RO)_3Si(CH_2)_nY$ can be used in particular, in which Y can provide the covalent or coordinative bond C with the component bonding substance X, R being an alkyl group with 1 ... 6 C-atoms, and n=1 ... 6. Y then comprises an active group such as a carboxylate, amino, pyridine derivative, imidazole, aldehyde, halogen, diazo, acid halide, azide, sulphonate, thioketone or hydroxyl group. An other coupler is a diazo compound such as

FIG. 4 shows the structural formulae of a number of compounds suitable for the bonding substance X, and FIG. 5 shows the reaction equations when using a coupler K for bonding a bonding substance X with OH groups of a $SiO_2$ substrate layer.

The following examples will provide a further elucidation of a practical realisation of the inventive idea.

EXAMPLE 1

Preparation of aminopropyl glass 3 wafers of Corning glass with a diameter of 40 mm and a thickness of 0,2 mm (about 2,7 g) were cleaned by a treatment in fuming nitric acid during 10 min. Subsequently said wafers were submerged in 150 ml water with 17 ml γ-aminopropyltriethoxysilane. The pH was adjusted at about 4 by means of 3N HCl. After 2 h heating at 75° C., the wafers were removed, washed with distilled water, and finally dried during 4 h at 120° C., and during 2 h at 150° C.

EXAMPLE 2

Preparation of N-(3-triethoxysilylpropyl)-p-nitrobenzamide p-nitrobenzoic acid (10 g; 60 mmol) was added to 15 g thionylchloride. This mixture was heated during 2 h under reflux. Subsequently the thionylchloride was removed at reduced pressure. To the remainder γ-aminopropyltriethoxysilane (13,3 g; 60 mmol) was added, dissolved in 50 ml diethylether with 10 g triethylamine. After 2 h agitation at room temperature, the mixture was filtered. The filtrate was evaporated at reduced pressure. The remainder was washed in water, filtered, and dried at reduced pressure over KOH. Yield: 9,5 g (43%). Melting point 99° ... 105° C.

EXAMPLE 3

Coupling of p-nitrobenzoic acid to alkylamine glass

A wafer of alkylamine glass of Example 1 was submerged in 150 ml 0,03M phosphoric acid (temperature 4° C.). Subsequently DCMI, 1-cyclohexyl-3-(2-morpholinoethyl)carbodimide-metho-p-toluenesulphonate (400 mg; 95 mmol) and p-nitrobenzoic acid (250 mg; 1,53 mmol) were added. After 16 h agitation, during which the temperature rose to room temperature, the wafer was removed, washed and dried at 100° C. The UV spectrum showed no perceptible absorption of the p-nitrobenzamide chromophore.

EXAMPLE 4

Coupling of N-(3-triethoxysilylpropyl)-p-nitrobenzamide to glass

By means of the method of Example 1, the benzamide of Example 2 was coupled to glass. The UV spectrum showed an absorption at 270 nm. The estimated load was 0,05 mmol/m².

EXAMPLE 5

Preparation of the N-(3-triethoxysilylpropyl)-amide of meso-tetra-(4-carboxyphenyl)-porphyrine Meso-tetra-(4-carbonxyphenyl)-porphyrine (0,59 g; 0.65 mmol) was added to 10 ml thionylchloride. This mixture was heated during 7 h at 80°. ... 90° C. Subsequently the thionylchloride was removed at reduced pressure. To the remainder γ-aminopropyotriethoxysilane (0,289 g; 1,26 mmol) was added, dissolved in 20 ml N,N-dimethylphormamide (DMF) with 1,5 ml triethylamine. After 6 h agitation at room temperature the mixture was filtered, and thereafter the filtrate was poured in 500 ml water at pH=2. After standing over night the obtained deep-green solid was filtered off and dried over $H_2SO_4$ at reduced pressure.

The yield was 0,15 g product, containing 1,5 ... 2,0 amide groups per porphyrine molecule.

EXAMPLE 6

Coupling of meso-tetra-(4-carboxyl)-porphyrine to alkylamine glass

By means of the method of Example 3 the meso-tetra(4-carboxyphenyl)-porphyrine was coupled to alkylamine glass. The derivatised glass showed a clearly dark hue in the visible range. The UV spectrum showed absorptions at 415 nm and 210 nm. The estimated loading was 0.06 mmol/m².

EXAMPLE 7

Coupling of the N-(3-triethoxysilylpropyl)-amide of meso-tetra(4-carboxyphenyl)-porphyrine to glass By means of the method of Example 1 the N-(3-triethoxysilylpropyl)-amide of meso-tetra(4-carboxyphenyl)-porphyrine of Example 5 was coupled to glass. The UV spectrum showed absorptions at 420 nm and 210 nm. The estimated loading was 0.08 mmol/m².

EXAMPLE 8

Preparation of the N-(3-triethoxysilylpropyl)-amide of Cu(II)-tetracarboxyphthalocyanine The acid chloride of Cu(II)-tetracarboxyphthalocyanine (200 mg; 0,2 mmol) was dissolved in 20 ml DMF which also contained 0,28 ml γ-aminopropylsilane and 1,5 ml triethylamine. The solution was agitated during 6 h, and was poured subsequently in 500 ml water at pH=1. The obtained blue solid was filtered off and dried. The yield was 200 mg product.

EXAMPLE 9

Coupling of Cu(II)-tettra(chloorcarboxyl)phthalocyanine to alkylamine glass

By means of the method of Example 3, the acid chloride of Cu(II)-tetracarboxyphthalocyanine was coupled to alkylamine glass. The UV spectrum showed absorptions at 600, 320 and 230 nm. The estimated loading was 0,57 mmol/m$^2$.

EXAMPLE 10

Coupling of the N-(3-triethoxysilylpropyl)-amide Cu(II)-tetracarboxyphthalocyanine to glass By means of the method of Example 1 the N-(3-triethoxysilylpropyl)-amide of Cu(II)-tetracarboxyphthalocyanine of Example 8 was coupled to glass. The UV spectrum showed absorptions at 320 and 230 nm. The estimated loading was 0,43 mmol/m$^2$.

The laboratory experiments described in the preceding examples have shown that the attachment according to the invention to substrates can be realised in the desired manner. In practice often preference will be given to substrates with surface layers of a pure oxide such as SiO$_2$ or ZnO instead of glass, but such layerrs will behave in the same manner as the examined glass wafers.

We claim:

1. A composite substrate for use in an apparatus for the quantitative detection of a substance present in a gas or liquid of the type having transducer means for inducing elastic vibrations in a surface layer of the substrate and detector means for sensing changes in the elastic vibrations resulting from bonding of the substance to be detected with the surface layer, the improvement wherein the surface layer (D') of said substrate (D) comprises a first substance having first active sites (A) adapted for covalent chemical bonding and molecules (X) of a second substance, said molecules (X) having at least one first active site forming a covalent bond with a respective active site (A) of said substrate (D'), and having at least one second active site (B) different from said first site, said second active sites (B) of said molecules (X) being adapted for selectively and reversibly making a coordinative bond with molecules (G) of the substance to be detected.

2. The substrate of claim 1, characterised in that said second substance (X) is an inclusion compound (X$_1$), activatable or non-activatable by metal ions, such as cyclodextrine or a crown ether; a complexing compound (X$_2$); a metal ion cluster (X$_3$); or an enzyme (X$_4$).

3. The substrate of claim 1, characterised in that the complexing compounds forming substance (X) is chosen on:
  (a) phthalocyanine compounds comprising H, Si or a metal ion;
  (b) porphryine compounds, with or without H, Si or a metal ion;
  (c) ferrocene compouns or this kind with an other metal; and
  (d) diketones or aminopolycarboxylates, comprising a metal ion such as a lanthanide ion.

4. A composite substrate for use in an apparatus for the quantitative detection of a substance present in a gas or liquid of the type having transducer means for inducing elastic vibrations in a surface layer of the substrate and detector means for sensing changes in the elastic vibrations resulting from bonding of the substance to be detected with the surface layer, the improvement wherein
 the surface layer (D') of said substrate (D) consists of a first substance having first active sites (A) adapted for covalent chemical bonding, coupling molecules (K) of a third substance each having at least one first active site adapted to form a covalent bond with a respective active site (A) of said first substance, and having at least one second active site adapted to form a second bond (C), and molecules (X) of a second substance, said molecules (X) having at least one first active site forming a bond with a second active site (C) of a respective coupling molecule (K), said molecules (X) having at least one second active site (B) in a point different from said first site said second active sites (B) of said molecules (X) being adapted for selective and reversible co-ordinative bonding with molecules (G) of the substance to be detected.

5. The substrate of claim 4, characterised in that said second bond is a substantially covalent bond.

6. The substrate of claim 4, characterised in that said second bond is a substantially coordinative bond.

7. The substrate of claim 1 or claim 4, characterised in that said substance (X) comprises one or more molecules each with a plurality of active sites (B).

8. The substrate of claim 1 or 4, characterized in that said surface layer comprises a material selected from the group of silicon dioxide (SiO$_2$) or a piezo-electric oxide such as zinc oxide (ZnO), and in that the active sites (A) of said surface layer are formed by OH-groups.

9. The substrate of claim 1, characterised in that the coupling molecule (K) is a trialkoxysilane compound with the general formula:

in which Y is adapted to provide the covalent or coordinative bond (C) with said second substance (X), and R is an alkyl group with between 1 and 6 C-atoms and n is a number between 1 and 6, Y comprising an active group selected from the group comprised of a carboxylate, an amino compound, a pyridine derivative, an imidazole, an aldehyde, a halogen, a diazo compound, an acid halogenide, an axide, a sulphonate, a thioketone or hydroxyl compound.

10. The substrate of claim 1, characterised in that said coupling molecule (K) is a compound selected from the group characterized by the formula:

* * * * *